United States Patent
Bennett et al.

(10) Patent No.: US 7,432,090 B2
(45) Date of Patent: Oct. 7, 2008

(54) BLOCKING SPORULATION BY INHIBITING SPOIIE

(75) Inventors: George N. Bennett, Houston, TX (US); Miles C. Scotcher, Seattle, WA (US)

(73) Assignee: Rice University, Houston, TX (US)

( * ) Notice: Subject to any disclaimer, the term of this patent is extended or adjusted under 35 U.S.C. 154(b) by 234 days.

(21) Appl. No.: 11/173,542

(22) Filed: Jul. 1, 2005

(65) Prior Publication Data

US 2007/0020740 A1      Jan. 25, 2007

Related U.S. Application Data

(60) Provisional application No. 60/584,727, filed on Jul. 1, 2004.

(51) Int. Cl.
C07H 21/02    (2006.01)
C07H 21/04    (2006.01)
C12P 7/00     (2006.01)
C12P 1/20     (2006.01)
C12Q 1/68     (2006.01)

(52) U.S. Cl. .................. 435/132; 435/6; 435/252.3; 435/252.7; 536/23.1; 536/24.1; 536/24.5

(58) Field of Classification Search .............. None
See application file for complete search history.

(56) References Cited

U.S. PATENT DOCUMENTS

2004/0248279 A1 * 12/2004 Sawada et al. ......... 435/252.31

OTHER PUBLICATIONS

Desai et al. Applied and Environmental Microbiology vol. 65(3): 936-945, Mar. 1999.*
Scothcer et al. Journal of Bacteriology vol. (6):1930-1936, Mar. 2005.*

* cited by examiner

Primary Examiner—Sean R McGarry
(74) Attorney, Agent, or Firm—Baker & McKenzie LLP

(57) ABSTRACT

We have shown that the control of solventogenesis and sporulation can be genetically uncoupled in *C. acetobutylicum*. In strain 824(pASspo), the absence of SpoIIE causes sporulation to be blocked at stage II. The cell remains in a vegetative state, and this allows solvent production to proceed for longer and for solvents to accumulate more rapidly and to a higher concentration. The characteristic drop in OD600 observed in wild type and control strains of *C. acetobutylicum* after 48-72 hours as the cells transition from the solventogenic phase to sporulation is notably absent in the fermentations of 824 (pASspo). Mutant S (wild type background, spoIIE disrupted), Mutant BS (Mutant B background, spoIIE disrupted), Mutant HS (Mutant H background, spoIIE disrupted) and Mutant bukS (buk- background, spoIIE disrupted) were generated to create stable solvent producing bacteria with complete inactivation of the SpoIIE protein. Similarity between the SpoIIE protein of *C. acetobutylicum, B. subtilis*, and other *Clostridial* species indicates that the techniques used in *C. acetobutylicum* can be applied to other solvent producing *Clostridia*.

13 Claims, 6 Drawing Sheets

Figure 1 – Antisense construct to spoIIE.

```
GATCcGCTCTTTCATATGTAATAACTTCACTATTATATAGCATATCAACATCCCCAATCTAAAAGTAATTACATTAc
    gCGAGAAAGTATACATTATTGAAGTGATAATATATCGTATAGTTGTAGGGGTTAGATTTTCATTAATGTAATgGATC
```

Figure 2 – CAT activity in strains 824(pMspo) and 824(pCATP).
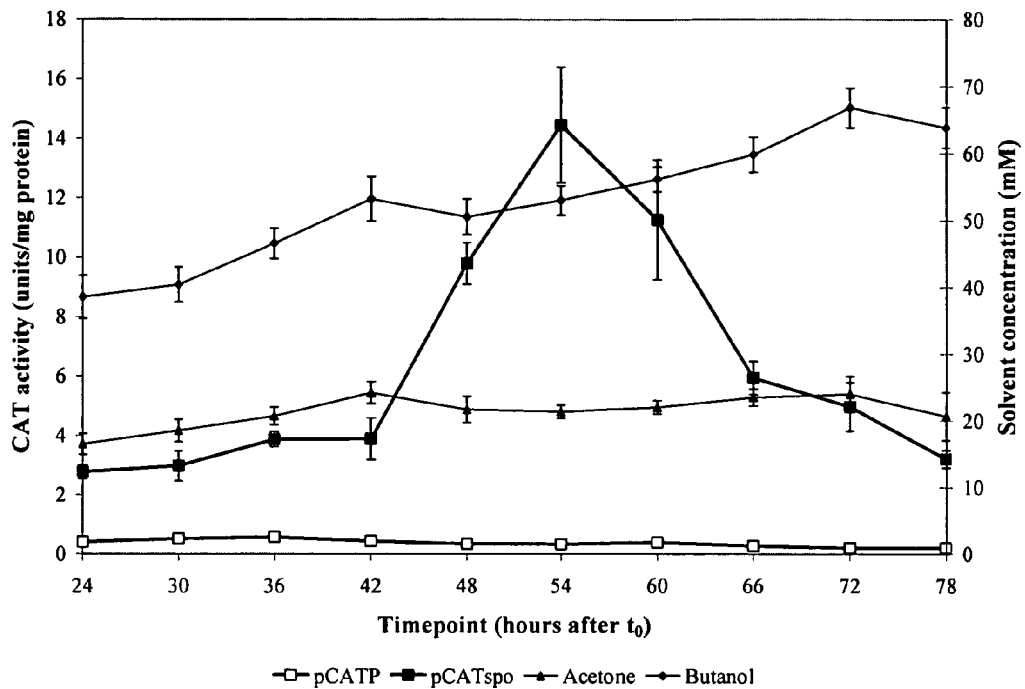
Figure 3 – β-galactosidase activity in 824(pTLspo) and SK(pTLspo).
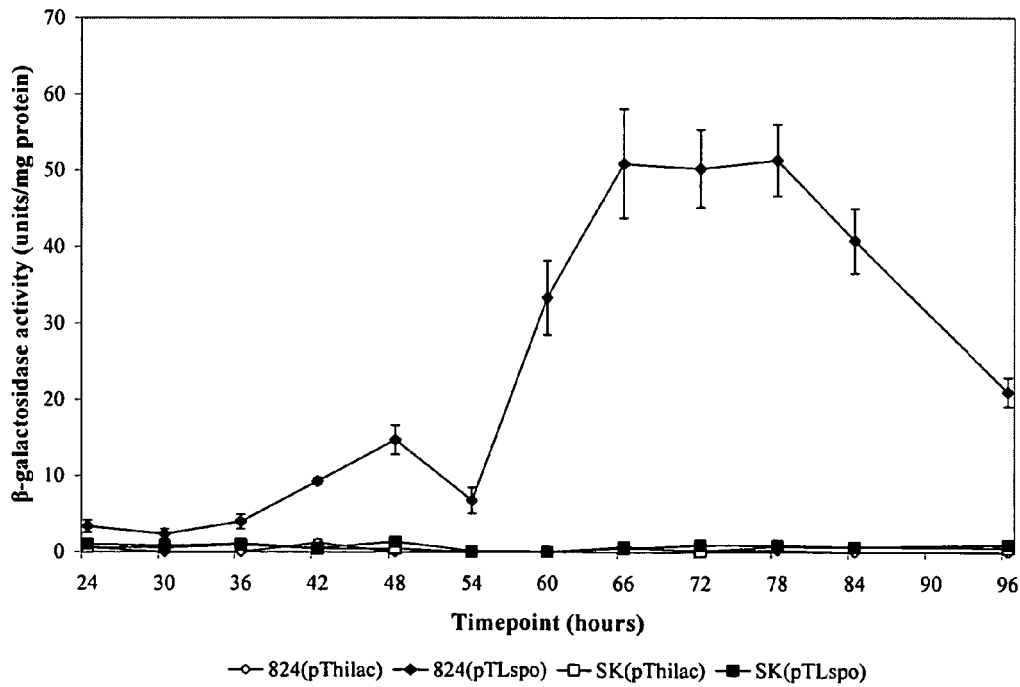

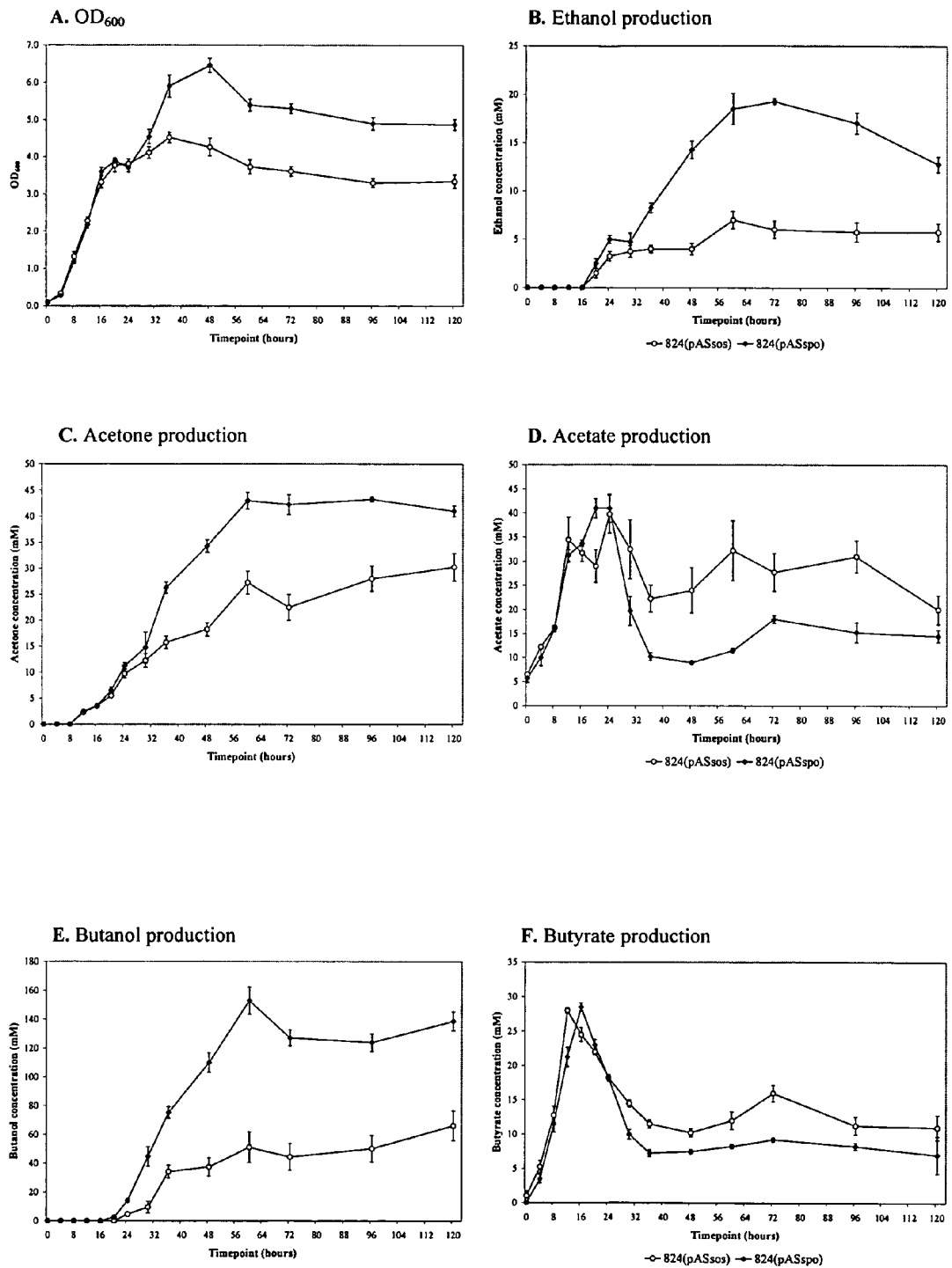
Figure 4 – Growth and product formation in strains 824(pASspo) and 824(pASsos).

Figure 5 – Phylogenetic tree of SpoIIE in different bacterial species.
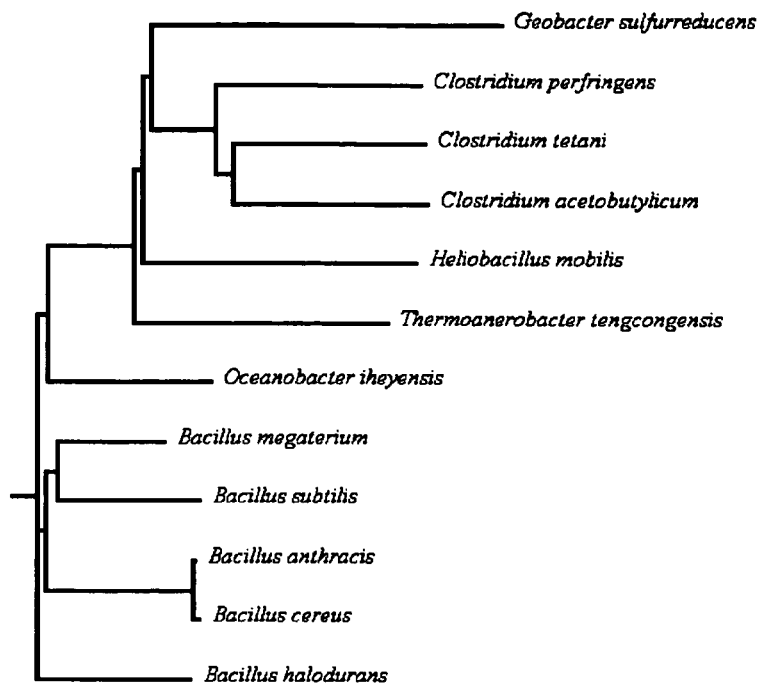
Figure 6 – Hydropathy plot of SpoIIE.
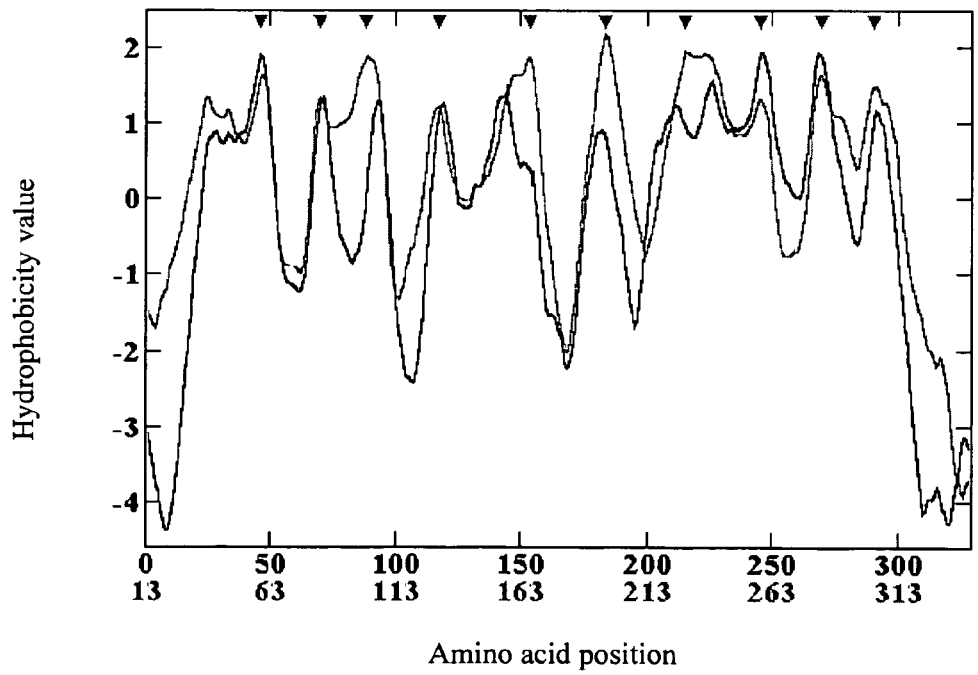

Figure 7 - Amino acid sequence alignment of SpoIIE in B. subtilis and C. acetobutylicum.

```
B. subtilis       539 EMTIPFSG-HGESEKIIAPMLSDILEEQILVKAEQHSPHENG-YSHVAFGSTKSYRMSTG
C. acetobutylicum 523 KITMEACGGRQICVKHVLEPINEAVGTLMCVGDEGCSICPETNLCSVTFEETPKYYTSSQ B. subtilis       597 AAHAAKGGLVSGDSYSMELGARKYAAAISDGMGNGARAHFESNETIKLLEKILESGID
C. acetobutylicum 583 IVRACKDGEEVNGDSYSFGKKDGNYNIISDGMGHGVLAEKESRAVIDLLEKENESSLN B. subtilis       657 EKIAINTINSILSLRTT-DEIMSTIDLSIIDIQDASCKFIKVGSTPSFIKRGDYMKVQA
C. acetobutylicum 643 RTMAINTMNSIMTLEFEEDEKESTMDLCSWDLYSGDAEFIKVGGVTSFIKKDKIEVINA B. subtilis       716 SNLPIGIINEFDMEVVSEQLKAGDLLIMMSDGIFEGPKHVENHDLNEKRKEKGLKTNDPR
C. acetobutylicum 703 KTLPIGVLFTVDMEVNHKKVENGDMIVMISDGWVNYDDENAGKVNIIDFLKNSSANKPK B. subtilis       776 ELAELLMEEVIRTRSGQIEDDMTVVVFRIDHNTPKWASIPVPAIFQNKQEIS 827
C. acetobutylicum 763 ELGEAMLKKAIELSGGKARDITITIIISKVYSLY------------------ 795
```

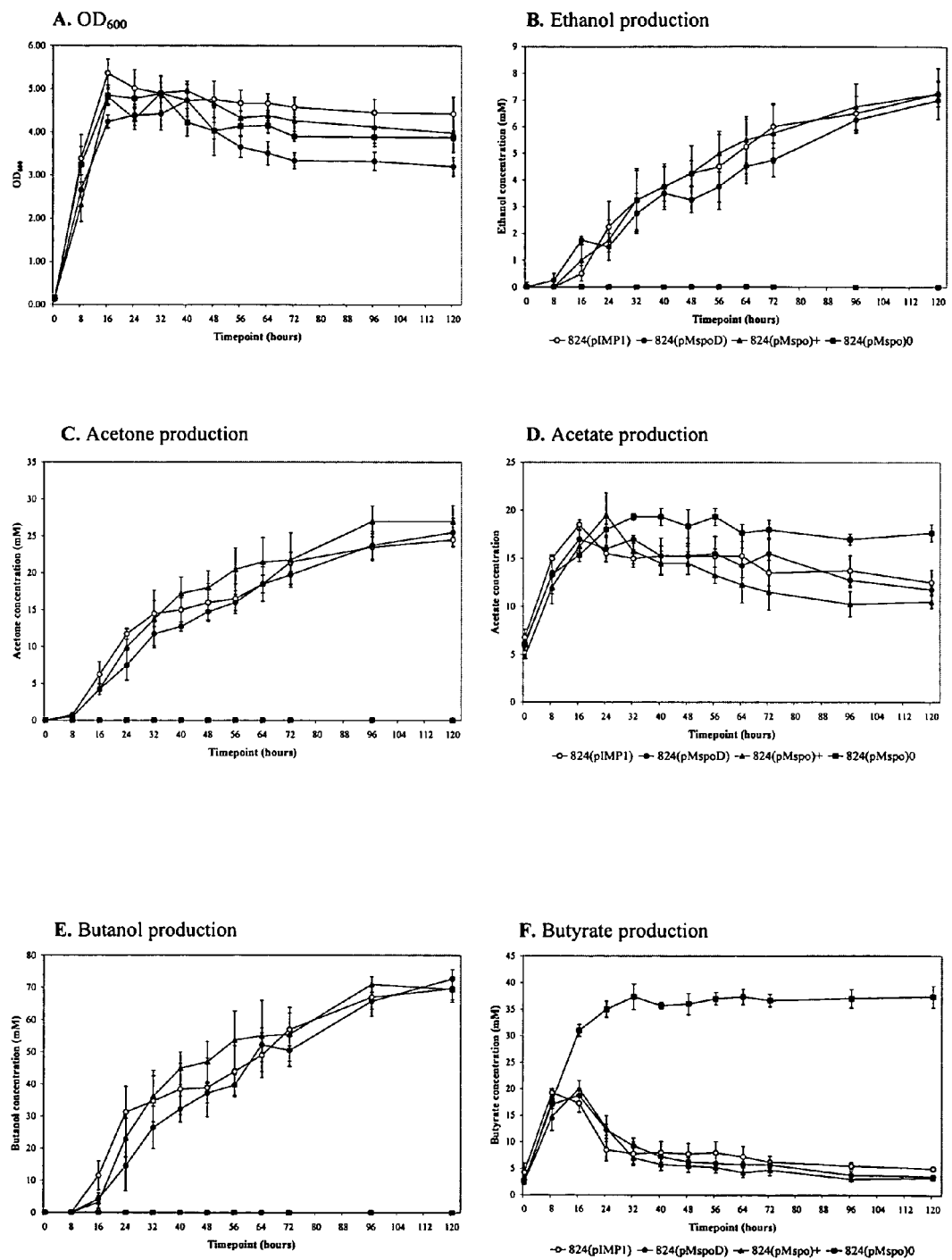
Figure 8 - Acid/solvent production in 120 hour 824(pMspo) fermentations.

BLOCKING SPORULATION BY INHIBITING SPOIIE

PRIOR RELATED APPLICATIONS

This application claims the benefit under 35 USC §119(e) to U.S. Provisional Application Ser. No. 60/584,727 filed Jul. 1, 2004, entitled "Blocking Sporulation by Inhibiting SPOIIE," which is incorporated herein in its entirety.

FEDERALLY SPONSORED RESEARCH STATEMENT

The present invention may have been developed with funds from the United States Government. Therefore, the United States Government may have certain rights in the invention.

REFERENCE TO MICROFICHE APPENDIX

Not applicable.

REFERENCE TO A SEQUENCE LISTING

A "Sequence Listing" with sequences labeled SEQ ID NO: 1-25 is attached hereto. A compact disc containing a Computer Readable Form (CRF) labeled "SEQUENCE LISTING.txt" is incorporated by reference. The copy in CRF is identical to the paper copy of the "Sequence Listing" submitted herewith.

FIELD OF THE INVENTION

The invention relates to the production of organic solvents in *Clostridium acetobutylicum*. Decreasing activity of the Stage II Sporulation Protein E (SpoIIE) increases solventogenesis in *Clostridia* by inhibiting sporulation without interfering with solvent production.

BACKGROUND OF THE INVENTION

The Gram-positive, obligate anaerobe *C. acetobutylicum* was used for the industrial production of the solvents acetone and butanol for over 60 years in the 20th century. With chemical synthesis of acetone and butanol proving significantly more economic, there are no industrial fermentation plants of *C. acetobutylicum* operational in the world today (11). However, over the last 20 years the genetics and biochemistry of *C. acetobutylicum* have been investigated in detail as we try to understand and improve upon the processes that control the production of solvents. Biological sources of organic solvents will become more economical as raw materials become more scarce or expensive and the need for renewable solvent sources increase.

Whereas much is known about the biochemistry of *C. acetobutylicum* metabolism and the genes and proteins that catalyze these processes, relatively little is known about the genetic control of the expression of these genes. Stage 0 Sporulation Protein A (Spo0A) controls both the onset of solventogenesis and the process of sporulation in *C. beijerinckii* and *C. acetobutylicum* (30, 20). In strain SKO1 of *C. acetobutylicum*, where Spo0A is deleted, acetone and butanol production is reduced to 2% and 8% of wild type levels respectively. Furthermore, SKO1 cells fail to sporulate and form extended filaments of conjoined rods (20).

Studies have also shown that there are a considerable number of *Bacillus subtilis* homologues in *C. acetobutylicum* including sigma factors and other proteins required for sporulation (32, 28). Although solventogenesis does not occur in *B. subtilis*, it appears that a cascade of sigma factors and stages similar to those involved in *B. subtilis* sporulation are present in *C. acetobutylicum*.

The control of solventogenesis in *C. acetobutylicum* is genetically linked to the control of sporulation, as shown by the Spo0A studies (30, 20). It has been suggested that solventogenesis and sporulation may be genetically uncoupled at some point during early sporulation (19), although as yet there are no reports of any attempts to do so. If solventogenesis could be genetically separated from sporulation, this would serve as an interesting and important illustration of the complexity of bacterial genetic control. Additionally, it may prove useful in bioengineering solvent producing strains of *Clostridium* for use in industry. A strain of *C. acetobutylicum* that underwent solventogenesis without entering sporulation would increase solvent production without inactivation, an ideal situation for large scale continuous fermentations.

SUMMARY OF THE INVENTION

*Clostridium* strains transformed with an antisense expression vector increased ethanol, acetone and butanol production by 225%, 43% and 110% respectively compared to the control strains. An antisense RNA vector targeted against spoIIE, designated pASspo was constructed and evaluated in various *C. acetobutylicum* strains. The genomic spoIIE gene was disrupted in *C. acetobutylicum* strains to generate Mutant S, Mutant BS, Mutant HS, and Mutant S buk-. These strains enable the stable production of solvents for continuous fermentation. Based on these experiments, a method of increasing solvent production was developed wherein a decrease in *Clostridial* SpoIIE activity inhibits sporulation while allowing continued solventogenesis, thus improving solvent yield.

As used herein Stage II Sporulation Protein E (SpoIIE) is used to refer to the spoIIE gene and SPOIIE gene product.

The term "isolated," as used herein, refers to a nucleic acid or polypeptide removed from its native environment. An example of an isolated protein is a protein bound by a polyclonal antibody, rinsed to remove cellular debris, and utilized without further processing. Salt-cut protein preparations, size-fractionated preparations, affinity-absorbed preparations, recombinant genes, recombinant protein, cell extracts from host cells that expressed the recombinant nucleic acid, media into which the recombinant protein has been secreted, and the like are also included. The term "isolated" is used because, for example, a protein bound to a solid support via another protein is at most 50% pure, yet isolated proteins are commonly and reliably used in the art.

The term "substantially purified," as used herein, refers to nucleic acid or protein sequences that are removed from their natural environment and are at least 75% pure. Preferably, at least 80, 85, or 90% purity is attained.

"Purified," as used herein refers to nucleic acids or polypeptides separated from their natural environment so that they are at least 95% of total nucleic acid or polypeptide in a given sample. Protein purity is assessed herein by SDS-PAGE and silver staining. Nucleic acid purity is assessed by agarose gel electrophoresis and EtBr staining.

The phrases "nucleic acid" or "nucleic acid sequence," as used herein, refers to polynucleotides, which may be cDNA or RNA and which may be single-stranded or double-stranded. The term also includes peptide nucleic acid (PNA), or to any chemically DNA-like or RNA-like material. "cDNA" refers to copy DNA made from mRNA that is naturally occurring in a cell. Combinations of the same are also possible (i.e., a recombinant nucleic acid that is part gDNA and part cDNA).

The term "oligonucleotide," as used herein, refers to a nucleic acid sequence of at least about 15 nucleotides to 100 nucleotides, and all integers between. Preferably, oligonucleotides are about 21 to 81 nucleotides, and most preferably about 51 to 78 nucleotides. Generally, an oligonucleotide must be greater than 21 to 27 nucleotides long for specificity, although shorter oligonucleotides will suffice in certain applications.

The term "antisense," as used herein, is a nucleic acid sequence complementary to a segment of genetic material (as mRNA) and serving to inhibit gene function. Antisense oligonucleotides can inhibit either transcription or translation and can be synthesized to include non-natural nucleotides. Furthermore, an antisense oligonucleotide can be recombinantly incorporated into a genomic, viral, or plasmid DNA and operably linked to a promoter for expression of the antisense oligonucleotide in vivo.

The terms "operably associated" or "operably linked," as used herein, refer to functionally coupled nucleic acid sequences.

The terms "disruption" and "disruption strains," as used herein, refer to cell strains in which the native gene is mutated, deleted, or interrupted in such a way as to decrease the activity of the protein.

"Reduced activity" of the SpoIIE protein is defined herein to be that reduction sufficient to inhibit sporulation. In a preferred embodiment, the reduction in activity is at least 75% as compared with control bacteria. Preferably, at least 80, 85, or 90% reduction in activity is attained. Use of a frame shift mutation, early stop codon, point mutations of critical residues, or deletions or insertions can completely inactivate (100%) gene product by completely preventing transcription and/or translation of active protein.

Alignments were performed using BLAST homology alignment as described by Tatusova & Madden (37) and available online at www.ncbi.nlm.nih.gov/BLAST/. The default parameters were used, except the filters were turned OFF. As of Jan. 1, 2001 the default parameters were as follows: BLASTN or BLASTP as appropriate; Matrix=none for BLASTN, BLOSUM62 for BLASTP; G Cost to open gap default=5 for nucleotides, 11 for proteins; E Cost to extend gap [Integer] default=2 for nucleotides, 1 for proteins; q Penalty for nucleotide mismatch [Integer] default=−3; r reward for nucleotide match [Integer] default=1; e expect value [Real] default=10; W wordsize [Integer] default=11 for nucleotides, 3 for proteins; y Dropoff (X) for blast extensions in bits (default if zero) default=20 for blastn, 7 for other programs; X dropoff value for gapped alignment (in bits) 30 for blastn, 15 for other programs; Z final X dropoff value for gapped alignment (in bits) 50 for blastn, 25 for other programs.

Abbreviations: $Ap^R$, ampicillin resistance cassette; cat, promoterless chloramphenicol acetyl transferase gene; catP, chloramphenicol acetyl transferase open reading frame with complete promoter; $Thi^R/Cm^R$, thiamphenicol/chloramphenicol resistance cassette with functional catP; $MLS^R$, macrolide, lincosamide and streptogramin A resistance cassette; $Str^R$, streptomycin resistance cassette; Ap, ampicillin; Em, erythromycin; Km, kanamycin; Cm, chloramphenicol; ColE1, Gram-negative origin of replication; OriII, repL, Gram-positive origin of replication; lacZ, promoterless β-galactosidase gene derived from *Thermoanaerobacterium thermosulfurogenes* EM1 (38); lacZ', truncated, non-functional copy of lacZ; mcrA, ΔmcrBC, methylcytosine-specific restriction system abolished; recA1, homologous recombination abolished; Spo0A$^-$, deletion of Spo0A. Common restriction enzymes and restriction sites can be found at NEB® (New England Biolabs®, www.neb.com) and Invitrogen® (www.invitrogen.com). ATCC®, American Type Culture Collection™(www.atcc.org).

BRIEF DESCRIPTION OF THE DRAWINGS

FIG. 1. Antisense construct to spoIIE. The spoIIE antisense construct consists of oligonucleotide "spoasastop" (SEQ ID NO: 22) and "spoasbtm" (SEQ ID NO: 23). The single underlined GATC forms the 5' BamHI "sticky" end. The black shaded region includes 38 bases of the spoIIE open reading frame, followed by 16 bases of the upstream leader sequence, shaded dark gray. The bold region forms the 17 base rho-independent terminator region from an antisense RNA targeted against the glnA gene, found naturally in *Clostridium saccharobutylicum* NCP262 (10).

FIG. 2. CAT activity in strain 824(pCATspo) (■) and control strain 824(pCATP) (□). The solvent levels are shown for acetone (▲) and butanol (♦). Data are shown ±1 standard error. For acetone and butanol, n=9; for 824(pCATP) CAT activity, n=3; for 824(pCATspo) CAT activity, n=6.

FIG. 3. β-galactosidase activity in strain 824(pTLspo) (♦) and control strains 824(pThilac) (◇), SK(pThilac) (□) and SK(pTLspo) (■). Data are shown ±1 standard error. For 824 (pThilac), 824(pTLspo) and SK(pTLspo), n=4; for SK(pThilac), n=3.

FIG. 4. Growth and product formation fermentations of strain 824(pASspo) (■) and strain 824(pASsos) (□). The name for each profile of and is shown above each graph. Data are shown ±1 standard error. For each data point, n=4.

FIG. 5. Phylogenetic tree of SpoIIE in different bacterial species. SpoIIE homologues shown are the 11 most identical to SpoIIE in *C. acetobutylicum*, as identified in a BLAST search of known bacterial genomes. Phylogenetic tree was generated using the Phylip™ format. Both BLAST and Phylip™ tools are available on the BiologyWorkbench™, located at workbench.sdsc.edu/ (San Diego Supercomputer Center, University of California—San Diego, Calif.).

FIG. 6. Hydropathy plot of SpoIIE. Hydropathy plots N-terminal region of SpoIIE from *B. subtilis* (gray line & X-axis scale) and *C. acetobutylicum* (black line & X-axis scale). Gray "▼" symbols at top of graph indicate transmembrane domains identified in SpoIIE of *B. subtilis* (2).

FIG. 7. Amino acid sequence alignment of SpoIIE in *B. subtilis* and *C. acetobutylicum*. Alignment was performed on the C-terminal amino acids of SpoIIE in *B. subtilis* (GenBank® Acc. # P37475) and *C. acetobutylicum* (GenBank® Acc. # NP 349801) using the CLUSTALW tool of the Biology Workbench (San Diego Supercomputer Center, University of California—San Diego, Calif.). Numbers indicate amino acid position. Background shading black=conserved residue; dark gray=conserved property; white background=no consensus. (28). Black "▼" symbols indicate the invariant D610, D628, D746, G747 and D795 in *B. subtilis*. Common motifs around the invariant D746, G747 and D795 are shown in boxes (9, 1).

FIG. 8. Acid/solvent production in 120 hour 824(pMspo) fermentations. Graphs for 120 hour fermentations of strains 824(pIMP1), 824(pMspoD) and 824(pMspo). The data for 824(pMspo) are therefore divided into those cultures which produced solvents, designated 824(pMspo)+, and those which did not, designated 824(pMspo)0. The data is arranged to allow comparison of growth and acid/solvent production between the 4 data sets as follows; A. Optical density (600 nm), B. Ethanol production, C. Acetone production, D.

Acetate production, E. Butanol production, F. Butyrate production. All data points are shown ±1 standard error. For 824(pIMP1), 824(pMspoD) and 824(pMspo)+, n=4; for 824 (pMspo)0, n=3.

DESCRIPTION OF EMBODIMENTS OF THE INVENTION

Methods for producing organic solvents are disclosed, one example of which is reducing SpoIIE activity in a solvent producing strain of *Clostridium* sufficiently to inhibit sporulation, culturing said strain under conditions suitable for solventogenesis, and purifying the solvents from the culture media.

Also provided are recombinant solvent producing *Clostridia* that have reduced SpoIIE protein activity sufficient to inhibit sporulation. Activity can be reduced 75%, 80%, 85%, 90%, or 95%. In a preferred embodiment the activity is reduced to essential nil. Such recombinant *Clostridium* can be engineered to produce antisense nucleotides to inhibit SpoIIE expression, or can be provided with SpoIIE mutations sufficient to inhibit activity. The mutations can be changes in the regulatory regions, premature stop codons, frame shift mutations, large insertions or deletions, or point mutations of invariant residues, but in an preferred embodiment, the mutation is a knock-out. Other methods of inhibiting SpoIIE activity can also be used.

Also provided are antisense oligonucleotides that function to decrease SpoIIE activity sufficiently to inhibit sporulation, without decreasing solventogenesis. Some examples are oligonucleotides comprising SEQ ID NO: 22, 23, 24, or 25. Also provided are mutant spoIIE gene sequences that can be used to create knock-strains or mutations that can be used to otherwise reduce SpoIIE activity.

*Escherichia coli* was grown in Luria-Bertani (LB) medium aerobically at 37° C. (26) appropriately supplemented with Ap at 100 µg/ml, Em at 200 µg/ml, Km at 50 µg/ml or Cm at 35 µg/ml. Strains were stored at −80° C. in medium supplemented with 50% glycerol. *C. acetobutylicum* strains were grown anaerobically in *Clostridial* Growth Medium (CGM) at 37° C. (21) appropriately supplemented with Em/Cm at 40 µg/ml or Thi at 25 µg/ml. Strains were stored as horse-serum supplemented lyophilized stocks at room temperature or at −80° C. in medium supplemented with 10% glycerol. For the sporulation and morphology assays, strains were grown on agar-solidified CBM supplemented with Em (40 µg/ml) anaerobically at 37° C (29).

EXAMPLE 1

Materials and Methods

TABLE 1

Strains and Plasmids

| Strain or plasmid | Relevant characteristics | Reference | ATCC # |
|---|---|---|---|
| *Strains* | | | |
| C. acetobutylicum | Wild type | ATCC ® | 824 |
| C. acetobutylicum SKO1 | spo0A−, MLS$^R$ | 20 | |
| E. coli DH10β | mcrA, ΔmcrBC, recAl, Str$^R$ | NEB ™ | |
| C. acetobutylicum MutS | ΔspoIIE, catP | this study | |
| C. acetobutylicum MutB | Mutant B (824 solR::pO1X) | 27 | |
| C. acetobutylicum MutBS | Mutant B ΔspoIIE, catP | this study | |
| C. acetobutylicum MutH | Mutant H (824 solR::pO1X) | 27 | |
| C. acetobutylicum MutHS | Mutant H ΔspoIIE, catP | this study | |
| C. acetobutylicum M5S | degenerated ΔspoIIE, catP | this study | |
| C. acetobutylicum buk- | Δ butyrate kinase | 15 | |
| C. acetobutylicum MutS buk- | Δ butyrate kinase, ΔspoIIE, catP | this study | |
| *Plasmids* | | | |
| pCATP | MLS$^R$, OriII, ColE1ori, catP | 34 | |
| pCATspo | MLS$^R$, OriII, ColE1ori, catP, spoIIE promoter | 35 | |
| pSA12 | MLS$^R$, OriII, ColE1ori, lacZ' | 43 | |
| pSC12lacZ | Cm$^R$, OriII, ColE1ori, lacZ' | 43 | |
| pHT3 | Ap$^R$, MLS$^R$, ColE1ori, repL, lacZ | 38 | |
| pThilac | Thi$^R$, OriII, ColE1ori, lacZ | 35 | |
| pTLspo | Thi$^R$, OriII, ColE1ori, lacZ, spoIIE promoter | 35 | |
| pIMP1 | Ap$^R$, MLS$^R$, ColE1ori, repL | 24 | |
| pMspo | Ap$^R$, MLS$^R$, ColE1ori, repL, spoIIE | 35 | |
| pMspoD | Ap$^R$, MLS$^R$, ColE1ori, repL, spoIIE' | 35 | |
| pSpoΔ4 | MLS$^R$, OriII, ColE1ori, lacZ', spoIIE | this study | |
| pSOS94 | ptb promoter, Ap$^R$, MLS$^R$, ColE1ori, repL | 38 | |
| pASsos | ptb promoter, Ap$^R$, MLS$^R$, ColE1ori, repL | 35 | |
| pASspo | ptb promoter, Ap$^R$, MLS$^R$, ColE1ori, repL | 35 | |

Plasmids were purified from *E. coli* using the QIAPREP™ Miniprep protocols. DNA was purified from agarose gels using the QIAQUICK™ Gel Extraction Kit, and PCR product or enzymatically-manipulated DNA was purified using the QIAQUICK™ PCR Purification Kit (QIAGEN™ Inc., Valencia, Calif.). Plasmids were purified from *C. acetobutylicum* according to the protocol developed by Harris (18). Genomic DNA was purified from *C. acetobutylicum* using the PUREGENE™ Genomic DNA Purification Kit (GENTRA SYSTEMS™, Minneapolis, Minn.).

All commercial enzymes used in this study (Taq polymerase, restriction endonucleases, calf intestinal phosphatases, T4 DNA ligase, Klenow fragment of DNA polymerase I) were used according to the manufacturers' recommendations.

Automated DNA sequencing was performed by LONESTAR™ automated DNA sequencing (LONESTAR LABORATORIES™ Inc., Houston, Tex., www.lslabs.com).

Prior to transformation into *C. acetobutylicum*, *E. coli* plasmid DNA was methylated by the phi3TI methyltransferase to prevent restriction by the *Clostridial* endonuclease Cac8241 (25). This was achieved by transformation of the required plasmid into DH10β *E. coli* harboring vector pDHKM (43) carrying an active copy of the phi3TI methyltransferase gene. Electrotransformation of methylated plasmids into *C. acetobutylicum* was carried out according to a modification of the protocol developed by Mermelstein (24). Positive transformants were isolated on agar-solidified CGM supplemented with the appropriate antibiotic, and transformations were confirmed by plasmid DNA purification.

A. CAT Assays

A chloramphenicol acetyl-transferase (CAT) reporter plasmid, pCATspo (35), was used to investigate expression patterns for the spoIIE gene in wild-type *Clostridium*. The pCATP plasmid (34) is the control without an spoIIE promoter construct. By operably linking the spoIIE promoter to the cat reporter protein, CAT activity in *C. acetobutylicum* strain 824(pCATspo) could be used to determine the expression patterns of the wild-type spoIIE gene and compare to the control strain 824(pCATP). FIG. 2 demonstrates that CAT expression (spoIIE promoter) increases at a uniform rate between 42 and 54 hours to a maximum of approximately 14

TABLE 2

SEQ ID NO AND DESCRIPTION

| SEQ ID NO: | TYPE | Length | Name and Description |
|---|---|---|---|
| 1 | DNA | 2388 nt | Wild type spoIIE cDNA [NC_003030 at 3351731 ... 3354118] |
| 2 | Peptide | 795 aa | Wild type SPOIIE protein [NP_349801] |
| 3 | DNA | 33 nt | spoprom - spoIIE primer |
| 4 | DNA | 35 nt | sporev - spoIIE primer |
| 5 | DNA | 42 nt | spofor - spoIIE primer |
| 6 | DNA | 30 nt | ASseq - automated sequencing primer |
| 7 | DNA | 25 nt | adhEleft - adhE primer |
| 8 | DNA | 25 nt | adhEright - adhE primer |
| 9 | DNA | 38 nt | sinRfor - sinR primer |
| 10 | DNA | 34 nt | sinRrev - sinR primer |
| 11 | DNA | 36 nt | spofragUP - Upstream spoIIE primer |
| 12 | DNA | 35 nt | spofragDS - Downstream spoIIE primer |
| 13 | DNA | 30 nt | catPstN - catP primer |
| 14 | DNA | 30 nt | catPstC - catP primer |
| 15 | DNA | 42 nt | spoORFfor - spoIIE ORF primer |
| 16 | DNA | 35 nt | spoORFrev - spoIIE ORF primer |
| 17 | DNA | 24 nt | bukDfor - butyrate kinase primer |
| 18 | DNA | 21 nt | bukDrev - butyrate kinase primer |
| 19 | DNA | 26 nt | solR453 - pO1X primer, solR primer |
| 20 | DNA | 23 nt | Tc238 - pO1X primer |
| 21 | DNA | 28 nt | solR1361 - solR primer |
| 22 | DNA | 77 nt | spoastop - spoIIE antisense oligonucleotide |
| 23 | DNA | 77 nt | spoasbtm - spoIIE antisense oligonucleotide |
| 24 | DNA | 54 nt | spoastop' - spoIIE antisense oligonucleotide |
| 25 | DNA | 54 nt | spoasbtm' - spoIIE antisense oligonucleotide |

All assays were conducted from single colonies of transformed *C. acetobutylicum* grown in closed-cap batch fermentations of 100 ml CGM supplemented with the appropriate antibiotic 37° C. in a FORMA SCIENTIFIC™ anaerobic chamber (THERMO FORMA™, Marietta, Ohio. To allow for differences in lag time following inoculation, zero hour (T0) was determined when the culture had reached an OD600 of 0.1. Fermentations were allowed to proceed for 120 hours.

EXAMPLE 2

Determining SpoIIE Expression Patterns

To investigate the role of SpoIIE in the control of solventogenesis and sporulation in *C. acetobutylicum*, initial studies focused on using the spoIIE promoter with a chloramphenicol acetyl-transferase (CAT) or β-galactosidase (β-Gal) reporter system to elucidate SPOIIE expression patterns. These experiments showed that spoIIE is expressed transiently in wild type *C. acetobutylicum* during mid- to late solventogenesis, but that there is no detectable expression of spoIIE in the spo0A-deleted mutant strain, SKO1. This agrees with reports that Sp0A is required for the transcriptional activation of spoIIE in *B. subtilis* (42), that spoIIE expression may be regulated by spoA, and that reduction of SPOIIE protein could be used to separate sporulation from solventogenesis.

units CAT/mg protein at 54 hours. Over the next 24 hours, the CAT activity returns to basal levels. Combined acetone and butanol concentrations from all cultures show that the individual cultures were in approximately the same stage of solventogenesis. These data show that the spoIIE promoter is active during mid- to late solventogenesis, which is the stage of growth where the cells are transitioning from vegetative growth to sporulation.

B. β-Gal Assays

A thiamphenicol-resistant lacZ reporter plasmid, pTLspo (35), was used to assay the spoIIE promoter activity in both wild-type and SKO1 (spoA-) *Clostridium*. Control plasmid pThilac (35) does not contain an spoIIE promoter. As with the CAT assay, fermentation products were assayed by gas chromatography to demonstrate that the individual cultures were in the same stages of solventogenesis. (data not shown). In both control strains 824(pThilac) and SK(pThilac), β-Gal activity was less than 1.2 unit/mg protein in any sample (data not shown). In strain 824(pTLspo), β-Gal activity is detectable during late solventogenesis, reaching a maximum of ~50 units/mg protein from 66 to 78 hours growth after T0. This is approximately 12 hours later than CAT activity in 824 (pCATspo). Additionally, β-Gal activity continues for over 48 hours, whereas CAT activity lasted 30 hours. These differences are a reflection of the variability in growth of *C. aceto-*

*butylicum*. β-Gal activity in SK(pTLspo) is not different from that observed in the control strains, and remains less than 1.3 units/mg protein in any sample indicating that spoIIE is not expressed in SKO 1.

These experiments indicate that *Clostridial* spoIIE expression occurs mid- to late solventogenesis, at which time the cell are expected to be transitioning between solventogenic growth and the onset of sporulation. SpoIIE expression was not observed in SKO1 (Spo0A-strain) we can conclude that, as in *B. subtilis*, Spo0A is required for the correct expression of spoIIE (42).

EXAMPLE 3

Product Formation with Increased SpoIIE

The SPOIIE expression vector pMspo (35) was generated to assess the effect of additional SPOIIE expression in wild-type *Clostridium*. The pMspo vector comprises the wild type spoIIE open reading frame including promoter. The pMspoD control plasmid (35) contains the upstream and downstream DNA (including promoter) with the open reading frame deleted. This ensures that effects seen in pMspo containing cells are not artifacts of the non-translated DNA sequences. Both constructs were generated in the $Am^R/MLS^R$ pIMP1 shuttle vector (24). *C. acetobutylicum* strain 824(pMspo) and the control strains 824(pIMP1) and strain 824(pMspoD) were generated by electrotransformation as described. In cultures of 824(pIMP1), 824(pMspoD) and 824(pMspo)+, product formation does not differ significantly between the strains. Acetone and butanol concentrations reach maximums of 25-27 mM and ~70 mM, which are typical for fermentations of this scale. After 120 hours, most of the acetate and butyrate has been reassimilated into acetone and butanol, leaving final concentrations of 10-12 mM acetate and less than 5 mM of butyrate. No ethanol, acetone or butanol is produced in cultures of 824(pMspo)0. This results in the accumulation of acids, and hence acetate and butyrate levels are elevated by ~33% and ~400% respectively, after 120 hours growth.

otides "spoastop" (SEQ ID NO: 22) and "spoasbtm" (SEQ ID NO: 23) were diluted to a concentration of 0.5 µg/µl. 9 µl of the "top" and 9 µl of the "btm" oligonucleotide were mixed with 2 µl of 10×STE buffer (100 mM Tris-HCl, 500mM NaCl, 10 mM EDTA, pH 8.0), and placed in a water bath set to 94° C. The water bath was allowed to cool to room temperature overnight, during which time the oligonucleotides annealed to form the antisense construct shown in FIG. 1. Vector pSOS94 (GenBank® Acc. # AY187685) was digested with BamHI and SfoI, and the 5.0 kb fragment was purified. This fragment was treated with the Klenow fragment of DNA polymerase I and self-ligated to form the control vector pASsos. The spoIIE antisense construct and the 5.0 kb fragment of pSOS94 were BamHI cohesive-end ligated, treated with the Klenow fragment of DNA polymerase I and self-ligated to form vector pASspo. Correct construction of pASsos and pASspo was confirmed by automated sequencing using primer "ASseq" (SEQ ID NO: 6) which hybridizes to pSOS94 between 148 and 118 bases upstream of the ptb promoter.

Growth and product formation in 120 hour fermentations of strains 824(pASsos) and 824(pASspo) is shown in FIG. 4. Cultures of 824(pASspo) grew significantly better than 824 (pASsos) with a maximum OD600 of ~6.5 compared to ~4.5. Maximum acetate concentrations in both strains were similar at ~40 mM after 24 hours growth. However, acetate levels decrease rapidly in 824(pASspo) as acetate is reassimilated into acetone, to a minimum of ~9 mM after 48 hours growth. Acetate production increases again after 48 hours, which coincides with acetone concentrations reaching a maximum of ~45 mM, at which they remain for the remainder of the fermentation. This is 50% greater than maximum acetone concentrations of ~30 mM observed in 824(pASsos) after 120 hours growth.

Butyrate production in both strains does not differ significantly, but this is not reflected in butanol production. In the

TABLE 3

PRODUCT FORMATION

| Strain | Ethanol (mM) | Acetone (mM) | Acetate (mM) | Butanol (mM) | Butyrate (mM) |
|---|---|---|---|---|---|
| 824 (pIMP1) | 7.25 ± 0.48 | 24.50 ± 0.87 | 12.50 ± 1.32 | 69.75 ± 3.50 | 5.00 ± 0.41 |
| 824 (pMspoD) | 7.00 ± 0.71 | 25.50 ± 1.94 | 11.75 ± 0.48 | 72.75 ± 2.93 | 3.50 ± 0.29 |
| 824 (pMspo)+ | 7.25 ± 0.95 | 27.00 ± 2.12 | 10.50 ± 0.65 | 69.50 ± 4.01 | 3.25 ± 0.48 |
| 824 (pMspo)0 | 0.00 ± 0.00 | 0.00 ± 0.00 | 17.67 ± 0.88 | 0.00 ± 0.00 | 37.33 ± 2.03 |

Using an α-amylase assay (35), it was determined that none of the cultures of 824(pIMP1), 824(pMspoD) and 824 (pMspo)+ were degenerate, but all three cultures of 824(pMspo)0 were degenerate and had lost the pSOL1 megaplasmid (7, 19, 31). This degeneration event required an intact copy of the spoIIE open reading frame, as none of the cultures of 824(pMspoD) degenerated. Thus increased levels of SPOIIE did not adversely affect solvent production but did cause degeneration of the pSOL1 megaplasmid.

EXAMPLE 5

Product Formation with SpoIIE Antisense

The antisense vector, pASspo, targeted against spoIIE was designed according to the method of Desai (10). Oligonuclecontrol strain, butanol production follows a typical pattern, reaching a maximum of ~66 mM after 120 hours growth. 824(pASspo) exhibits a rapid increase in butanol production between 16 and 64 hours growth, at which timepoint butanol production remains constant for the remainder of the fermentation. A maximum butanol concentration of ~153 mM was recorded in 824(pASspo), which is a 132% increase compared to the control strain.

By decreasing SPOIIE activity using an antisense oligonucleotide expressed from the pASspo plasmid, the *Clostridia* spent a greater amount of time undergoing solventogenesis, were able to reproduce to a higher density of cells, and inhibit sporulation. The overall effect of reducing SPOIIE activity is a drastic increase in solvent production from engineered solvent producing *Clostridia*.

EXAMPLE 6

Morphology and Sporulation

Strains harboring pASsos and pASspo were grown simultaneously were observed at 24, 48, 72 and 140 hour intervals. At 24 hours growth, both strains are morphologically similar with cells are visible in all stages of division, and in neither strain are sporulating cells observed. After 48 hours growth, many 824(pASspo) cells can be seen dividing, whereas majority of 824(pASsos) cells are single rods with the occasional sporulating cell. After 72 hours, many 824(pASsos) cells can be seen to be sporulating, but there are still some 824(pASspo) cells that are in the process of division. Additionally, some single cells have an abnormal morphology, such that they are elongated two- to threefold compared to the control. Examination of several different cultures of 824 (pASspo) indicated that these elongated cells are common, and that they were not mis-identified as vegetative cells undergoing division. After 140 hours growth, sporulating cells or free endospores dominated the 824(pASsos) culture, with very few vegetative cells observed. In contrast, very few sporulating cells were observed in cultures of 824(pASspo), with the majority of cells appearing to be in the vegetative growth state. Of those cells which were sporulating, there were several types of abnormal morphology that could be observed. These experiments indicate that the antisense DNA was properly expressed, decreased SPOIIE activity, and inhibited, delayed or drastically reduced the cells ability to undergo sporulation.

EXAMPLE 7

SpoIIE-Disrupted Strains

The plasmid pSpoΔ4 was constructed from a fragment of spoIIE (bases 3351731 through 3354118 of the *C. acetobutylicum* genome, GENBANK® Acc. # NC_003030). DNA spanning from the 509th base to the 1113th base of the open reading frame was amplified by PCR using primers "spofragUP" (SEQ ID NO: 11; containing an EcoRI restriction site) and "spofragDS" (SEQ ID NO: 12; containing an XbaI restriction site). Vector pSA12 and the spoIIE fragment were digested with EcoRI and XbaI, and ligated to form plasmid pPreSpoΔ4. The ~0.9 kb catP gene was PCR amplified by from plasmid pIMPTH (16) using primers "catPstN"(SEQ ID NO: 13) and "catPstC" (SEQ ID NO: 14) both primers contain PstI restriction sites. A PstI restriction site was located in the centre of the spoIIE fragment. Vector pPreSpoΔ4 and the catP gene were digested with PstI and ligated to form vector pSpoΔ4. Correct construction of pSpoΔ4 was confirmed by sequencing with primers "spofragUP" (SEQ ID NO: 11) and "spofragDS" (SEQ ID NO: 12). The plasmid pSpoΔ4 was electrotransformed into *C. acetobutylicum* according to standard protocol. Positive transformants of wild type cells were selected on Em media and transformants of Mutants B, H and buk- selected on Em/Thi media. Single colonies of positive transformants were grown up overnight in CGM supplemented with Em. 20 µl was streaked on RCM plates, and allowed to grow for 48 hours prior to replica plating onto fresh RCM plates. Replica plating was carried out 5 times. Additionally, 20 µl from the original cultures was streaked on CGM containing Em, Thi, and Thi/Em to confirm that the pSpoΔ4 plasmid was not lost from the Em-resistant mutant strains.

A final replica plating was performed to transfer colonies onto CGM supplemented with Thi. 10 colonies of each strain were grown up for further testing. All colonies were tested by purification of the genome and PCR amplification used to confirm both the strain background and the correct insertion of the spoIIE disruption cassette. Genomic DNA was purified using PUREGENE® Genomic DNA Purification Kit from (Gentra Systems, Minneapolis, Minn.). The MASTERTAQ® PCR kit (EPPENDORF®) was used for all PCRs.

TABLE 4

PCR PRODUCT CONFIRMS DISRUPTION

| Primer 1: | SEQ ID NO. | Primer 2 | SEQ ID NO. | Wild-type | Mutant product |
|---|---|---|---|---|---|
| spoORFfor | 15 | spoORFrev | 15 | 2.4 kb | 3.3 kb spoIIE-strain |
| spoORFfor | 15 | catPstN | 13 | Null | 1.7 kb spoIIE-strain |
| bukDfor | 17 | bukDrev | 18 | 0.9 kb | 5.5 buk-strain |
| solR453 | 19 | Tc238 | 20 | Null | 2.1 kb pO1X (Mut B and Mut H) 7 kb MutH |
| solR453 | 19 | solR1361 | 21 | 0.9 kb | Null Mut B |
| adhEleft | 7 | adhEright | 8 | 2.9 kb pSOL1 | Null = degenerate |
| sinRfor | 9 | sinRrev | 10 | Genomic control | |

Mutants disrupted for spoIIE were identified in all background strains, and were named Mutant S (wild type background, spoIIE disrupted), Mutant BS (Mutant B background, spoIIE disrupted), Mutant HS (Mutant H background, spoIIE disrupted) and Mutant bukS (buk-background, spoIIE disrupted). Additionally, one strain of Mutant S degenerated and this was called Mutant M5S. This strain will be characterized as compared to Mutant S and also M5. *C. acetobutylicum* strains with disrupted SpoIIE genes provide an ideal strain for continuous fermentation and batch production of solvents. It is expected that the cells harboring a genomic disruption of the spoIIE knockout will provide a more stable cell strain and provide a complete inactivation of the SPOIIE protein. It is also predicted that this will dramatically increase solvent production using these strains.

EXAMPLE 8

SpoIIE-homologues

The gene designated CAC3205 in *C. acetobutylicum* has been identified as SpoIIE (28, GENBANK® Acc. # NC_003030). The SPOIIE cDNA and protein can be found at SEQ ID NO: 1 and 2. Phylogenetic analysis of the SPOIIE protein sequences verifies isolation of the SpoIIE sequence and identifies SPOIIE as a target in other solvent producing *Clostridia*. FIG. 5 shows a phylogenetic tree of *C. acetobutylicum* SPOIIE and its 11 closest relatives from other bacterial species. The *B. subtilis* SpoIIE is not the closest relative to SpoIIE in *C. acetobutylicum*, and as expected, the SpoIIE protein from related *Clostridium* are more closely related than the *B. subtilis* protein. Therefore methods performed using the *C. acetobutylicum* SpoIIE cDNA and protein may be used in other related solvent producing *Clostridia*.

Although *B. subtilis* do not undergo solventogenesis, the hydropathy plots in FIG. 6 indicate the two *Clostridia* and *Bacillus* SPOIIE proteins do have some similar properties and structures. *B. subtilis* SPOIIE consists of two distinct regions—an N-terminal hydrophobic region that crosses the membrane 10 times, and the C-terminal, cytoplasmic catalytic domain (9). The superimposed plots for SpoIIE in *B. subtilis* and *C. acetobutylicum* indicate similar regions of hydrophobicity and hydrophilicity, suggesting that the N-terminus of SpoIIE in *C. acetobutylicum* forms a similar membrane 10-spanning region. The C-terminal catalytic domain of SpoIIE in *C. acetobutylicum* also exhibits conservation of critical amino acids as shown in FIG. 7. The asp-610 and asp-628 residues have been shown to be conserved throughout a range of bacterial and eukaryotic PP2C-like phosphatases, and form a metal ion binding pocket within the active site of human PP2C (9). The two conserved regions surrounding the invariant asp-746, gly-747 and asp-795 have also been identified in SpoIIE homologues and PP2C phosphatases in *S. pombe*, cow, mouse, human and *A. thaliana*. Mutation of these invariant residues to alanine also causes a severe decrease in sporulation efficiency in *B. subtilis* (1, 33). All the invariant amino acids conserved between *Bacillus* and *Clostridial* SpoIIE are essential and can be used to inactivate the SPOIIE protein in any number of solventogenic *Clostridia*.

We have shown that the control of solventogenesis and sporulation can be genetically uncoupled in *C. acetobutylicum*. In strain 824(pASspo), the absence of SpoIIE causes sporulation to be blocked at stage II. The cell remains in a vegetative state, and this allows solvent production to proceed for longer and for solvents to accumulate more rapidly and to a higher concentration. The characteristic drop in OD600 observed in wild type and control strains of *C. acetobutylicum* after 48-72 hours as the cells transition from the solventogenic phase to sporulation is notably absent in the fermentations of 824(pASspo). Mutant S (wild type background, spoIIE disrupted), Mutant BS (Mutant B background, spoIIE disrupted), Mutant HS (Mutant H background, spoIIE disrupted) and Mutant bukS (buk- background, spoIIE disrupted) were generated to create stable solvent producing bacteria with complete inactivation of the SpoIIE protein. Similarity between the SpoIIE protein of *C. acetobutylicum*, *B. subtilis*, and other *Clostridial* species indicates that the techniques used in *C. acetobutylicum* can be applied to other solvent producing *Clostridia*.

All of the references cited herein are expressly incorporated by reference. References are listed again here for convenience:

1. Adler, et al. Mol. Microbiol. 23:57-62 (1997).
2. Arigoni, et al. Science 270:637-40 (1995).
3. Arigoni, et al. Mol. Microbiol. 31:1407-15 (1999).
4. Ben-Yehuda and Losick. Cell 109:257-66 (2002).
5. Bork, et al. Protein Sci. 5:1421-5 (1996).
6. Bradford. Anal Biochem 72:248-54 (1976).
7. Cornillot, et al. J. Bact. 179:5442-5447 (1997).
8. Davison, et al. Microbiology 141:989-96 (1995).
9. Das, et al. EMBO J. 15:6798-809 (1996).
10. Desai and Papoutsakis. Appl. Environ. Microbiol. 65:936-45 (1999).
11. Dürre, P. 2001. From Pandora's box to Cornucopia: Clostridia—A Historical Perspective. In P. Dürre and H. Bahl (ed.), *Clostridia*—Biotechnology and Medical Applications. Wiley-VCH, New York, N.Y. (2001)
12. Feucht, et al. Mol. Microbiol. 33:1015-26 (1999).
13. Feucht, et al. Mol Microbiol. 45:1119-30 (2002).
14. Frandsen, et al. Genes Dev 13:394-9 (1999).
15. Green, et al. Microbiology. 142:2079-86 (1996).
16. Green and Bennett. Biotechnol. Bioeng. 58:215-21 (1998).
17. Guzman, et al. J. Bact. 170:1598-609 (1988).
18. Harris, L. M. Fermentation characterization of *Clostridium acetobutylicum* ATCC824 recombinant strains. MSc Thesis. Northwestern University, Evanston, Ill. (1997).
19. Harris, L. M. 2001. Cloning and characterization of the *Clostridium acetobutylicum* ATCC824 gene encoding the Spo0A transcription regulator and its role in controlling solvent formation and sporulation-specific gene expression. PhD Thesis. Northwestern University, Evanston, Ill. (2001).
20. Harris, et al. J. Bact. 184:3586-97 (2002).
21. Hartmanis and Gatenbeck. Appl. Environ. Microbiol. 47:1277-83 (1984).
22. Kroos, et al. Mol. Microbiol. 31:1285-94 (1999).
23. Lucet, et al. EMBO J. 19:1467-75 (2000).
24. Mermelstein, et al. Bio/Technology 10:190-195 (1992).
25. Mermelstein and Papoutsakis. Appl. Environ. Microbiol. 59:1077-1081 (1993).
26. Miller, J. H. Experiments in molecular genetics. Cold Spring Harbor Laboratory Press, Cold Spring Harbor, N.Y. (1972).
27. Nair, et al. J. Bact. 181:319-30 (1999).
28. Nöling, et al. J. Bact. 183:4823-38 (2001).
29. O'Brien and Morris. J. Gen. Microbiol. 68:307-18 (1971).
30. Ravagnani, et al. Mol. Microbiol. 37:1172-85 (2000).
31. Sabathe, et al. FEMS Microbiol. Lett. 210:93-8 (2002).
32. Santangelo, et al. FEMS Microbiol. Lett. 161:157-64 (1998).
33. Schroeter, et al. FEMS Microbiol. Lett. 174:117-23 (1999).
34. Scotcher, et al. J. Ind. Microbiol. Biotechnol. 30:414-20 (2003).
35. Scotcher and Bennett. J. Bact. 187:1930-6 (2005).
36. Shaw. Methods Enzymol. 43:737-55 (1975).
37. Tatusova and Madden. FEMS Microbiol. Lett. 174:247-50 (1999).
38. Tummala, et al. Appl. Environ. Microbiol. 65:3793-9 (1999).
39. Tummala, et al. J. Bact. 185:1923-34 (2003).
40. Tummala, et al. J. Bact. 185:3644-53 (2003).
41. Wong and Bennett. Curr. Microbiol. 32:349-56 (1996).
42. York, et al. J. Bact. 174:2648-58 (1992).
43. Zhao, et al. Appl. Environ. Microbiol. 69:2831-41 (2003).
44. Zhao, et al. Appl. Environ. Microbiol. 71:530-7 (2005).

What is claimed is:

1. A method for producing organic solvents comprising:
   a) culturing a solvent producing strain of *Clostridium* having reduced SpoIIE activity, wherein said SpoIIE activity is reduced by an antisense oligonucleotide, under conditions suitable for solventogenesis to generate a culture media; and
   b) purifying solvents from said culture media.

2. The method of claim 1, wherein said antisense oligonucleotide is expressed from a plasmid.

3. The method of claim 1, wherein said antisense oligonucleotide comprises a nucleotide sequence selected from the group consisting of SEQ ID NO: 22, 23, 24, and 25.

4. A recombinant solvent producing *Clostridium* having reduced SpoIIE activity sufficient to inhibit sporulation, wherein said SpoIIE activity is reduced by an antisense oligonucleotide directed against an SpoIIE gene and wherein said reduced SpoIIE activity increases the production of ethanol, acetone, and/or butanol from a pSOL1 megaplasmid.

5. The solvent producing *Clostridium* of claim 4, wherein said antisense oligonucleotide is expressed from a plasmid.

6. The solvent producing *Clostridium* of claim 4, wherein said plasmid is pASspo.

7. The solvent producing *Clostridium* of claim 4, wherein said antisense oligonucleotide comprises a nucleotide sequence selected from the group consisting of SEQ ID NO: 22, 23, 24, and 25.

8. The solvent producing *Clostridium* of claim 4 selected from the group consisting of Mutant B, Mutant H, Mutant buk-, *acetobutylicum,* and *acetobutylicum* ATCC 824.

9. The solvent producing *Clostridium* strain of claim 8, selected from the group consisting of 824(pASspo), SK(pASspo), Mutant B (pASspo), Mutant H (pASspo), and Mutant buk- (pASspo).

10. The solvent producing *Clostridium* strain of claim 4 selected from the group consisting of Mutant S, Mutant BS, Mutant HS and Mutant bukS comprising an antisense oligonucleotide expressed from a plasmid.

11. An antisense oligonucleotide comprising a nucleotide sequence selected from the group consisting of SEQ ID NO: 22, 23, 24, and 25.

12. A genetically engineered *Clostridium* having reduced activity of stage II sporulation protein E (SpoIIE) sufficient to inhibit sporulation, wherein said SpoIIE activity is reduced by an antisense comprising a sequence selected from the group consisting of SEQ ID NO: 22, 23, 24, and 25, wherein said *Clostridium* is selected from the group consisting of Mutant B, Mutant H, Mutant buk-, acetobutylicum, acetobutylicum ATCC 824, 824(pASspo), SK(pASspo), Mutant B (pASspo), Mutant H (pASspo), and Mutant buk- (pASspo), and wherein said reduced SpoIIE activity results in increased solvent production from a pSOL1 megaplasmid.

13. A genetically engineered *Clostridium* having reduced activity of stage II sporulation protein E (SpoIIE) sufficient to inhibit sporulation, wherein said SpoIIE activity is reduced by an antisense comprising a sequence selected from the group consisting of SEQ ID NO: 22, 23, 24, and 25 and wherein said reduced SpoIIE activity results in increased solvent production.

* * * * *

UNITED STATES PATENT AND TRADEMARK OFFICE
CERTIFICATE OF CORRECTION

PATENT NO. : 7,432,090 B2
APPLICATION NO. : 11/173542
DATED : October 7, 2008
INVENTOR(S) : George N. Bennett and Miles C. Scotcher It is certified that error appears in the above-identified patent and that said Letters Patent is hereby corrected as shown below:

Column 1 Lines 15 to 16 - Replace the sentence "Therefore, the United States Government may have certain rights in the invention." with -- Therefore, the United States Government and the National Science Foundation, under Grant No. BES-0001288, may have certain rights in the invention. --

Signed and Sealed this

Eighteenth Day of August, 2009

David J. Kappos
*Director of the United States Patent and Trademark Office*

SEQUENCE LISTING

<160> NUMBER OF SEQ ID NOS: 25

<210> SEQ ID NO 1
<211> LENGTH: 2388
<212> TYPE: DNA
<213> ORGANISM: Clostridium acetobutylicum

<400> SEQUENCE: 1

```
atgctatata atagtgaagt tattacatat gaaagagcac ctaaatcaga aaaagataca      60
aaagtagaaa atataaaaaa actatttata ttaaaagtat taatttatgc agtgagttca     120
tttgctataa gtagagttgt aatgataaat tctatggtac cattcggaat agcttttta     180
gcatgcgttt aatatataa gaagaatgat aaagcttcgt ttttagcagc tgtgggaagt     240
ttggttggtt atatatcgat tagcggtgaa gtgaaagata gcgttatgta tgagattggt     300
gtaattatta ttacgctgct tatggtggtt atgaaagaaa aagaagatat aaagaagtta     360
gtaacttcgg caatattttt attgatagaa tttattatgt ttaaaatact tgttgaaaaa     420
ttaacagtac aatcagcact tatatttact ttaattgaga tagcatgtgt ttgttcagta     480
tattatatta ttaggtatgg aattatatgc cttgataaca taagaacaaa acatcttttt     540
acaaatgaag atataataag catgtcagtt ttggtggctt tagttatttc aggaacaaga     600
aattttgata tttataatgt atcgataaga aacgttttag ctatggtttt tgtaattgct     660
atttcatata tagagggaag ttcagcagga gcagctggtg gtattgctat tggagcaatc     720
attggtatga atagcagcga tgtaatgatt tatataggag tatttggatt tttaggattt     780
atagcaggag tttttaagga ttttggaaag tggattactg caggagtata tcttattata     840
tttttgataa taattattta ttgtaagaat catgttgatt ttagcctaat ggaagcagct     900
ataacatgta ttatatttgc ggggatacct aataagcttt acaagaaaat ggagtgtgag     960
tttaattggg atagaaagca atcagatatt actaatagat atattgaaaa gatgaaggat    1020
atttttgtta aaaagcttga gaatttttca gaagttttgt ttacaatgtc tactacccta    1080
aataatcttg ctgacaatga caaacttaca atgaagaata agagttgcag actagttgaa    1140
aatttggccg atagagtatg cggaaagtgt aatatgaact caatatgctg gaaaagagag    1200
atatattata cttatgcagc cttcgaagag cttatacaaa attttcagga gggtataaat    1260
aaaattcctg atgagattga gagaaaatgt gtcaggagaa aagagcttat aaagcatacg    1320
gacatgataa taaatgacta taatgaac gagatgtgga gaatgcaggt atgcagtgga    1380
agagaattta tgtccgctca ggttaagaat ataggtacat ctgttgagaa tataatagat    1440
gaatttagca tgaattaaa gtttaatgtt gatgtagagg agaaaataat aagattgcta    1500
aataagatgg ggataccata taaggatata atgtgtgtaa atgataaaag aaacagaaat    1560
cttgtaaagc ttcaatggga agcgtgtggg ggaagacaga tttgtgttaa acatgtactt    1620
ccagttatta atgaggctgt aggaacgctt atgtgtgtag agatgatgg atgcagtata    1680
tgtccagaaa ctaattatg cagtgttact tttgaggaga cgcctaagta ttatatatcc    1740
tcacaaatag taagagcttg caaagatggt gaagaggtaa atggcgatag ttatagcttt    1800
ggaaaaggaa aagatggaaa ctataatata ataataagtg atggtatggg acatggagtt    1860
caagcggaaa agaaagtag agcagttatt gatttaatag aaaaatttaa tgaatcaagt    1920
cttaatagaa ctatggctat aaatacagtt aactctataa tgacgcttaa atttgaagaa    1980
gatgagaaat tttcaacggt agatttgtgt agcgtggatt tatactctgg tgatgctgaa    2040
```

-continued

```
tttataaagg ttggaggagt aacaagtttt ataaagaaaa aagataaaat tgaagttata    2100
aatgctaaga cacttcctat aggagtactt gatacagttg atatggaggt taatcacaag    2160
aaggttgaaa atggagacat gatagtaatg ataagtgatg cgtagttaa ttatgatgac     2220 gagaatgctg aaaagtaaa ttggataata gattttctta aaaatagtag tgcaaataag     2280
cctaaagagt taggagaagc tatgctaaaa aaagctatag aactttctgg tggaaaagca    2340
aaggatgata taaccataat aatttctaaa gtatacagct tatattaa                 2388
```

<210> SEQ ID NO 2
<211> LENGTH: 795
<212> TYPE: PRT
<213> ORGANISM: Clostridium acetobutylicum

<400> SEQUENCE: 2

```
Met Leu Tyr Asn Ser Glu Val Ile Thr Tyr Glu Arg Ala Pro Lys Ser
 1               5                  10                  15

Glu Lys Asp Thr Lys Val Glu Asn Ile Lys Lys Leu Phe Ile Leu Lys
            20                  25                  30

Val Leu Ile Tyr Ala Val Ser Ser Phe Ala Ile Ser Arg Val Val Met
        35                  40                  45

Ile Asn Ser Met Val Pro Phe Gly Ile Ala Phe Leu Ala Cys Val Leu
    50                  55                  60

Ile Tyr Lys Lys Asn Asp Lys Ala Ser Phe Leu Ala Ala Val Gly Ser
65                  70                  75                  80

Leu Val Gly Tyr Ile Ser Ile Ser Gly Glu Val Lys Asp Ser Val Met
                85                  90                  95

Tyr Glu Ile Gly Val Ile Ile Thr Leu Leu Met Val Val Met Lys
            100                 105                 110

Glu Lys Glu Asp Ile Lys Lys Leu Val Thr Ser Ala Ile Phe Leu Leu
        115                 120                 125

Ile Glu Phe Ile Met Phe Lys Ile Leu Val Glu Lys Leu Thr Val Gln
    130                 135                 140

Ser Ala Leu Ile Phe Thr Leu Ile Glu Ile Ala Cys Val Cys Ser Val
145                 150                 155                 160

Tyr Tyr Ile Ile Arg Tyr Gly Ile Ile Cys Leu Asp Asn Ile Arg Thr
                165                 170                 175

Lys His Leu Phe Thr Asn Glu Glu Ile Ile Ser Met Ser Val Leu Val
            180                 185                 190

Ala Leu Val Ile Ser Gly Thr Arg Asn Phe Asp Ile Tyr Asn Val Ser
        195                 200                 205

Ile Arg Asn Val Leu Ala Met Val Phe Val Ile Ala Ile Ser Tyr Ile
    210                 215                 220

Glu Gly Ser Ser Ala Gly Ala Ala Gly Gly Ile Ala Ile Gly Ala Ile
225                 230                 235                 240

Ile Gly Met Asn Ser Ser Asp Val Met Ile Tyr Ile Gly Val Phe Gly
                245                 250                 255

Phe Leu Gly Phe Ile Ala Gly Val Phe Lys Asp Phe Gly Lys Trp Ile
            260                 265                 270

Thr Ala Gly Val Tyr Leu Ile Ile Phe Leu Ile Ile Ile Tyr Cys
        275                 280                 285

Lys Asn His Val Asp Phe Ser Leu Met Glu Ala Ala Ile Thr Cys Ile
    290                 295                 300

Ile Phe Ala Gly Ile Pro Asn Lys Leu Tyr Lys Lys Met Glu Cys Glu
```

-continued

```
            305                 310                 315                 320
Phe Asn Trp Asp Arg Lys Gln Ser Asp Ile Thr Asn Arg Tyr Ile Glu
                325                 330                 335

Lys Met Lys Asp Ile Phe Val Lys Lys Leu Glu Asn Phe Ser Glu Val
                340                 345                 350

Leu Phe Thr Met Ser Thr Thr Leu Asn Asn Leu Ala Asp Asn Asp Lys
                355                 360                 365

Leu Thr Met Lys Asn Lys Ser Cys Arg Leu Val Glu Asn Leu Ala Asp
                370                 375                 380

Arg Val Cys Gly Lys Cys Asn Met Asn Ser Ile Cys Trp Lys Arg Glu
385                 390                 395                 400

Ile Tyr Tyr Thr Tyr Ala Ala Phe Glu Glu Leu Ile Gln Asn Phe Gln
                405                 410                 415

Glu Gly Ile Asn Lys Ile Pro Asp Glu Ile Glu Arg Lys Cys Val Arg
                420                 425                 430

Arg Lys Glu Leu Ile Lys His Thr Asp Met Ile Ile Asn Asp Tyr Ile
                435                 440                 445

Met Asn Glu Met Trp Arg Met Gln Val Cys Ser Gly Arg Glu Phe Met
                450                 455                 460

Ser Ala Gln Val Lys Asn Ile Gly Thr Ser Val Glu Asn Ile Ile Asp
465                 470                 475                 480

Glu Phe Ser Asn Glu Leu Lys Phe Asn Val Asp Val Glu Glu Lys Ile
                485                 490                 495

Ile Arg Leu Leu Asn Lys Met Gly Ile Pro Tyr Lys Asp Ile Met Cys
                500                 505                 510

Val Asn Asp Lys Arg Asn Arg Asn Leu Val Lys Leu Thr Met Glu Ala
                515                 520                 525

Cys Gly Gly Arg Gln Ile Cys Val Lys His Val Leu Pro Val Ile Asn
                530                 535                 540

Glu Ala Val Gly Thr Leu Met Cys Val Gly Asp Asp Gly Cys Ser Ile
545                 550                 555                 560

Cys Pro Glu Thr Asn Leu Cys Ser Val Thr Phe Glu Glu Thr Pro Lys
                565                 570                 575

Tyr Tyr Ile Ser Ser Gln Ile Val Arg Ala Cys Lys Asp Gly Glu Glu
                580                 585                 590

Val Asn Gly Asp Ser Tyr Ser Phe Gly Lys Gly Lys Asp Gly Asn Tyr
                595                 600                 605

Asn Ile Ile Ile Ser Asp Gly Met Gly His Gly Val Gln Ala Glu Lys
                610                 615                 620

Glu Ser Arg Ala Val Ile Asp Leu Ile Glu Lys Phe Asn Glu Ser Ser
625                 630                 635                 640

Leu Asn Arg Thr Met Ala Ile Asn Thr Val Asn Ser Ile Met Thr Leu
                645                 650                 655

Lys Phe Glu Glu Asp Glu Lys Phe Ser Thr Val Asp Leu Cys Ser Val
                660                 665                 670

Asp Leu Tyr Ser Gly Asp Ala Glu Phe Ile Lys Val Gly Gly Val Thr
                675                 680                 685

Ser Phe Ile Lys Lys Lys Asp Lys Ile Glu Val Ile Asn Ala Lys Thr
                690                 695                 700

Leu Pro Ile Gly Val Leu Asp Thr Val Asp Met Glu Val Asn His Lys
705                 710                 715                 720

Lys Val Glu Asn Gly Asp Met Ile Val Met Ile Ser Asp Gly Val Val
                725                 730                 735
```

```
Asn Tyr Asp Asp Glu Asn Ala Gly Lys Val Asn Trp Ile Ile Asp Phe
        740                 745                 750

Leu Lys Asn Ser Ser Ala Asn Lys Pro Lys Glu Leu Gly Glu Ala Met
    755                 760                 765

Leu Lys Lys Ala Ile Glu Leu Ser Gly Gly Lys Ala Lys Asp Asp Ile
    770                 775                 780

Thr Ile Ile Ile Ser Lys Val Tyr Ser Leu Tyr
785                 790                 795

<210> SEQ ID NO 3
<211> LENGTH: 33
<212> TYPE: DNA
<213> ORGANISM: Artificial
<220> FEATURE:
<223> OTHER INFORMATION: Primer

<400> SEQUENCE: 3
ccgggatcca tcaacatccc caatctataa acc                              33

<210> SEQ ID NO 4
<211> LENGTH: 35
<212> TYPE: DNA
<213> ORGANISM: Artificial
<220> FEATURE:
<223> OTHER INFORMATION: Primer

<400> SEQUENCE: 4
agcggatcca cactaccaag tcaagaagct ttcac                            35

<210> SEQ ID NO 5
<211> LENGTH: 42
<212> TYPE: DNA
<213> ORGANISM: Artificial
<220> FEATURE:
<223> OTHER INFORMATION: Primer

<400> SEQUENCE: 5
agcggatcca catattgata acatcattta tcaacaaaaa ca                    42

<210> SEQ ID NO 6
<211> LENGTH: 30
<212> TYPE: DNA
<213> ORGANISM: Artificial
<220> FEATURE:
<223> OTHER INFORMATION: Primer

<400> SEQUENCE: 6
ttacgaagta aataagtcta gtgtgttaga                                  30

<210> SEQ ID NO 7
<211> LENGTH: 25
<212> TYPE: DNA
<213> ORGANISM: Artificial
<220> FEATURE:
<223> OTHER INFORMATION: Primer

<400> SEQUENCE: 7
aatataatag gttggataga tgaac                                       25

<210> SEQ ID NO 8
<211> LENGTH: 25
<212> TYPE: DNA
<213> ORGANISM: Artificial
<220> FEATURE:
```

<223> OTHER INFORMATION: Primer

<400> SEQUENCE: 8
tttgttaatt aagagatcta cctttt 25

<210> SEQ ID NO 9
<211> LENGTH: 38
<212> TYPE: DNA
<213> ORGANISM: Artificial
<220> FEATURE:
<223> OTHER INFORMATION: Primer

<400> SEQUENCE: 9
agcggatcca catgttatca atccattcca ttaacatc 38

<210> SEQ ID NO 10
<211> LENGTH: 34
<212> TYPE: DNA
<213> ORGANISM: Artificial
<220> FEATURE:
<223> OTHER INFORMATION: Primer

<400> SEQUENCE: 10
agcggatcca cacaatttct tcgcctccct atac 34

<210> SEQ ID NO 11
<211> LENGTH: 36
<212> TYPE: DNA
<213> ORGANISM: Artificial
<220> FEATURE:
<223> OTHER INFORMATION: Primer

<400> SEQUENCE: 11
ccggaattcg ccttgataac ataagaacaa aacatc 36

<210> SEQ ID NO 12
<211> LENGTH: 35
<212> TYPE: DNA
<213> ORGANISM: Artificial
<220> FEATURE:
<223> OTHER INFORMATION: Primer

<400> SEQUENCE: 12
gctctagaca ttgtaagttt gtcattgtca gcaag 35

<210> SEQ ID NO 13
<211> LENGTH: 30
<212> TYPE: DNA
<213> ORGANISM: Artificial
<220> FEATURE:
<223> OTHER INFORMATION: Primer

<400> SEQUENCE: 13
atactgcagc ggcaagtgtt caagaagtta 30

<210> SEQ ID NO 14
<211> LENGTH: 30
<212> TYPE: DNA
<213> ORGANISM: Artificial
<220> FEATURE:
<223> OTHER INFORMATION: Primer

<400> SEQUENCE: 14
atactgcagg gtctttgtac taacctgtgg 30

```
<210> SEQ ID NO 15
<211> LENGTH: 42
<212> TYPE: DNA
<213> ORGANISM: Artificial
<220> FEATURE:
<223> OTHER INFORMATION: Primer

<400> SEQUENCE: 15
agcggatcca catattgata acatcattta tcaacaaaaa ca                42

<210> SEQ ID NO 16
<211> LENGTH: 35
<212> TYPE: DNA
<213> ORGANISM: Artificial
<220> FEATURE:
<223> OTHER INFORMATION: Primer

<400> SEQUENCE: 16
agcggatcca cactaccaag tcaagaagct ttcac                       35

<210> SEQ ID NO 17
<211> LENGTH: 24
<212> TYPE: DNA
<213> ORGANISM: Artificial
<220> FEATURE:
<223> OTHER INFORMATION: Primer

<400> SEQUENCE: 17
tgcaagaagt tcatcttctc cacc                                   24

<210> SEQ ID NO 18
<211> LENGTH: 21
<212> TYPE: DNA
<213> ORGANISM: Artificial
<220> FEATURE:
<223> OTHER INFORMATION: Primer

<400> SEQUENCE: 18
ctcgacctca actaaaattg g                                      21

<210> SEQ ID NO 19
<211> LENGTH: 26
<212> TYPE: DNA
<213> ORGANISM: Artificial
<220> FEATURE:
<223> OTHER INFORMATION: Primer

<400> SEQUENCE: 19
gagttgaatt tagcatgaat ttatta                                 26

<210> SEQ ID NO 20
<211> LENGTH: 23
<212> TYPE: DNA
<213> ORGANISM: Artificial
<220> FEATURE:
<223> OTHER INFORMATION: Primer

<400> SEQUENCE: 20
catagaaatt gcatcaacgc ata                                    23

<210> SEQ ID NO 21
<211> LENGTH: 28
<212> TYPE: DNA
<213> ORGANISM: Artificial
<220> FEATURE:
<223> OTHER INFORMATION: Primer
```

-continued

```
<400> SEQUENCE: 21
aattttccgt taagtatttt tttatcat                                          28

<210> SEQ ID NO 22
<211> LENGTH: 77
<212> TYPE: DNA
<213> ORGANISM: Artificial
<220> FEATURE:
<223> OTHER INFORMATION: Oligonucleotide

<400> SEQUENCE: 22
gatccgctct ttcatatgta ataacttcac tattatatag catatcaaca tccccaatct       60
aaaagtaatt acattac                                                      77

<210> SEQ ID NO 23
<211> LENGTH: 77
<212> TYPE: DNA
<213> ORGANISM: Artificial
<220> FEATURE:
<223> OTHER INFORMATION: Oligonucleotide

<400> SEQUENCE: 23
gcgagaaagt atacattatt gaagtgataa tatatcgtat agttgtaggg gttagatttt       60
cattaatgta atggatc                                                      77

<210> SEQ ID NO 24
<211> LENGTH: 54
<212> TYPE: DNA
<213> ORGANISM: Artificial
<220> FEATURE:
<223> OTHER INFORMATION: Oligonucleotide

<400> SEQUENCE: 24
gctctttcat atgtaataac ttcactatta tatagcatat caacatcccc aatc             54

<210> SEQ ID NO 25
<211> LENGTH: 54
<212> TYPE: DNA
<213> ORGANISM: Artificial
<220> FEATURE:
<223> OTHER INFORMATION: Oligonucleotide

<400> SEQUENCE: 25
cgagaaagta tacattattg aagtgataat atatcgtata gttgtagggg ttag             54
```